(12) United States Patent
Lupin et al.

(10) Patent No.: US 7,033,313 B2
(45) Date of Patent: Apr. 25, 2006

(54) SURGICALLY IMPLANTABLE HEARING AID

(75) Inventors: Alan J. Lupin, Victoria (CA); Ewa J. Lupin, Victoria (CA)

(73) Assignee: No. 182 Corporate Ventures Ltd., Vancouver (CA)

( * ) Notice: Subject to any disclaimer, the term of this patent is extended or adjusted under 35 U.S.C. 154(b) by 0 days.

(21) Appl. No.: 10/316,066

(22) Filed: Dec. 11, 2002

(65) Prior Publication Data

US 2004/0116772 A1   Jun. 17, 2004

(51) Int. Cl.
*H04R 25/00* (2006.01)

(52) U.S. Cl. ..................................... 600/25

(58) Field of Classification Search .............. 600/25; 181/128–137; 381/68–69.2, 312–331; 607/55–57; 128/898
See application file for complete search history.

(56) References Cited

U.S. PATENT DOCUMENTS

| 2,402,392 | A | * | 6/1946 | Goldschmidt | ............... 381/418 |
| 4,606,329 | A | | 8/1986 | Hough | |
| 4,612,915 | A | * | 9/1986 | Hough et al. | ................. 600/25 |
| 4,982,434 | A | * | 1/1991 | Lenhardt et al. | ............. 381/326 |
| 4,988,333 | A | * | 1/1991 | Engebretson et al. | ......... 600/25 |
| 5,047,994 | A | * | 9/1991 | Lenhardt et al. | ............. 367/116 |
| 5,558,618 | A | | 9/1996 | Maniglia | |
| 5,772,575 | A | | 6/1998 | Lesinski et al. | |
| 5,800,336 | A | | 9/1998 | Ball et al. | |
| 5,859,916 | A | * | 1/1999 | Ball et al. | ................... 381/326 |
| 6,277,148 | B1 | | 8/2001 | Dormer | |
| 2001/0003288 | A1 | | 6/2001 | Ball et al. | |
| 2002/0173697 | A1 | * | 11/2002 | Lenhardt | ..................... 600/25 |
| 2004/0032962 | A1 | * | 2/2004 | Westerkull | .................. 381/151 |

FOREIGN PATENT DOCUMENTS

EP          0 263 254          4/1988

OTHER PUBLICATIONS

Sichel, J-Y., New Approach for Implantable Hearing Aids: A Feasibility Study, Annals of Otology, Rhinology and Laryngology 2004:936-940.

* cited by examiner

*Primary Examiner*—Samuel G. Gilbert
(74) *Attorney, Agent, or Firm*—Oyen Wiggs Green & Mutala LLP

(57) ABSTRACT

The invention comprises a surgically implantable hearing aid for hearing impaired persons. The hearing aid includes a vibrational element which is vibrated by sound waves and attached to the skull of the person, and a connector which crosses the mastoid cavity and delivers the sound waves to the dura mater of the patient thereby vibrating the dura mater, the cerebrospinal fluids, and the brain to create a hearing percept. The invention can also be adapted to act as a tinnitus masker or used in conjunction with a cochlear implant. It can also be used in a modified form to connect directly through the skull of the person.

2 Claims, 7 Drawing Sheets

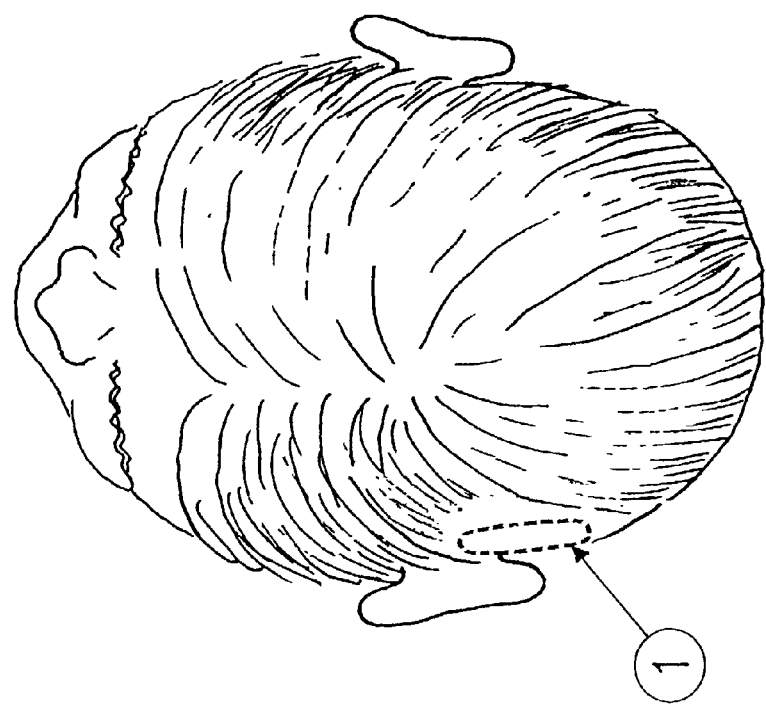
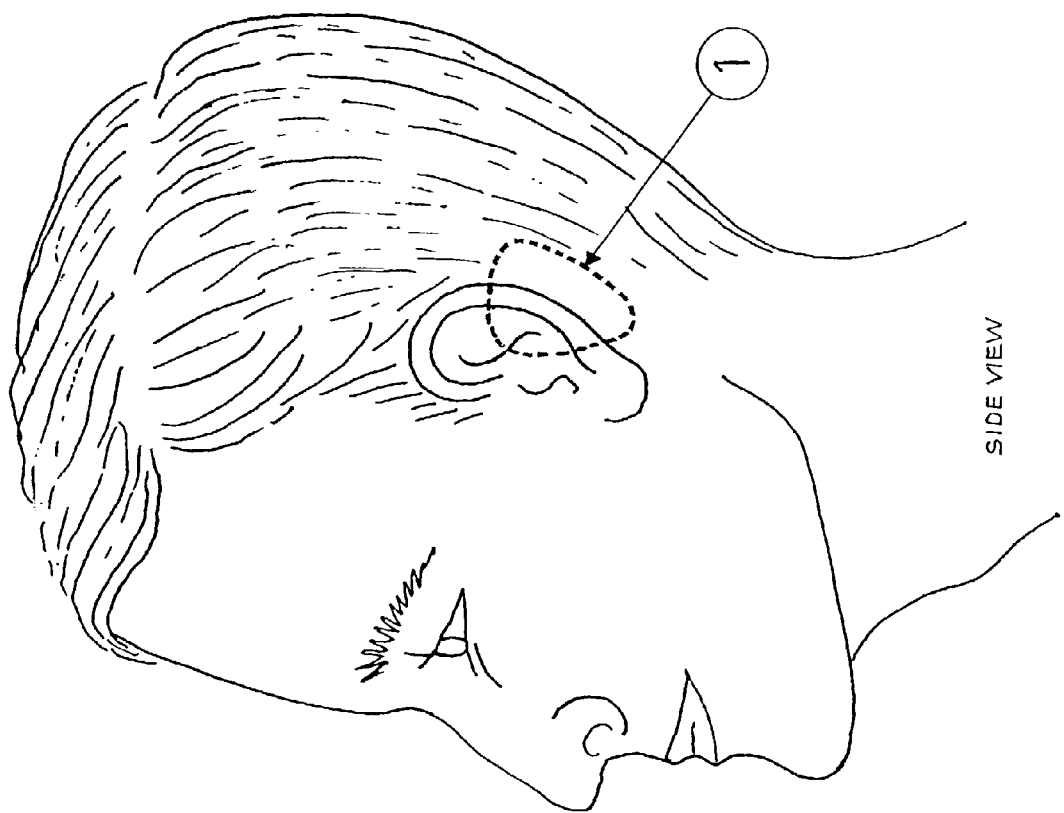
Fig 1a SIDE VIEW
Fig 1b PLAN VIEW

SURGICALLY IMPLANTABLE HEARING AID

FIELD OF THE INVENTION

The invention relates to a surgically implantable hearing aid to treat persons with deafness, tinnitus or a combination of these ailments. More particularly, this invention pertains to a surgically implantable hearing aid that stimulates directly through the dura mater to the cerebrospinal fluid and the brain of the person.

BACKGROUND OF THE INVENTION

Hearing loss occurs in approximately 1 in 10 North Americans and in approximately one in ten of these persons, it is classified as profound.

Tinnitus or "ringing" noises in the ears are perceived by about 20% of the population in North America. Approximately 1 million persons in the U.S. alone are experiencing sufficiently severe tinnitus that it impairs their ability to cope with daily life.

Hearing aids for deaf persons have been getting smaller and their function has improved with advances in technology. Great changes have occurred over the years, advancing from the nineteenth century "ear trumpet" to small devices which fit in the ear canal and are not visible externally. A logical development is to implant the aid surgically.

A number of patents are relevant or of interest. Ball et al. in U.S. Pat. No. 5,800,336, describe a "floating mass transducer" with an electromagnet attached to one of the middle ear bones, the incus, such that it drives the ossicular chain. U.S. Pat. No. 5,558,618, Magnilia, describes a device consisting of a magnet mounted to the ossicular chain driven by an implanted electromagnetic coil. Dormer, in U.S. Pat. No. 6,277,148, describes a middle ear magnet driven by a coil placed in the external auditory canal, and Lesinski et. al., in U.S. Pat. No. 5,772,575, describe another vibrating piezoelectric device for direct stimulation of the ossicles.

Most surgically implantable hearing aids suffer among other things from the disadvantage that they involve altering or connection to the ossicles or small bones of the middle ear and these bones are very fragile with tenuous blood supply so that the pressure on these ossicles from any direction leads to halisterisis or dissolving of the bone at the point of attachment. This phenomenon occurs either immediately or over a short period of time.

A second disadvantage of implantable hearing aids that connect to the ossicles is that the surgery is complicated and delicate, which allows the possibility of damage to the middle ear membranes, or blood supply or to adjacent structures such as the facial nerve.

A third disadvantage is that the production of vibratory forces via the ossicles or through the middle ear causes sound to exit the ear via the tympanic membrane. This frequently gives rise to auditory feedback or "squealing" which is familiar to users of in-the-ear hearing aids.

There is thus a strong need for a hearing aid device that does not damage the middle ear or ossicles, can be implanted surgically with minimum damage to the surrounding structures, for example the facial nerve, and which, by design, does not cause auditory feedback.

Tinnitus maskers are devices that produce a sound external to the sufferer and distract the sufferer from hearing the internal noise that is currently believed to be in the brain itself. In this respect, this device could be affected electronically to produce a percept for a tinnitus patient that achieves this result.

The use of an implantable aid with a cochlear implant is becoming more common as new cochlear implant surgical techniques frequently use gentle surgery that leaves existing hearing intact.

SUMMARY OF THE INVENTION

The invention comprises a surgically implantable hearing aid for hearing impaired persons. The hearing aid includes a vibrational element attached to the skull of the person by a bracket, a connector which crosses the mastoid cavity and a pad which touches the dura mater and delivers vibrational sound waves directly to the dura mater of the patient thereby vibrating the dura mater, the cerebrospinal fluids, and the brain to create a hearing percept. The invention can also be adapted to act as a tinnitus masker or used in conjunction with a cochlear implant. It can also be used in a modified form to connect straight through the skull of the person.

In one embodiment, the invention relates to a device which can be implanted in the head of a mammal and can transmit sound waves external to the head into the inner ear of the mammal directly through the dura mater, the cerebrospinal fluid and the brain of the mammal. The mammal can be a human being.

The device which can be implanted in the head of a human being can comprise a sound wave receiving microphone which converts the sound waves into electrical impulses and transmits the electrical impulses to a transducer, which converts the electrical impulses to mechanical vibrations which are transmitted directly to the dura mater, cerebrospinal fluid and the brain to the inner ear of a person.

The invention also relates to a surgically implantable apparatus comprising: (a) a microphone which receives sound waves and converts them to electric signals; (b) a vibrating assembly or transducer which converts the electric signals to produce mechanical vibrations driven either electromagnetically or by piezoelectric forces or by other means; (c) a connecting bracket which attaches to the skull of a person over the mastoid cavity and supports the vibrating assembly or transducer; (d) a connecting mechanism which transfers the mechanical vibrations directly to the dura mater of the interior of the skull of the person; (e) wires which interconnect the vibrating assembly or transducer to at least one hermetic housing containing electronics or a battery; and (f) at least one coil for receiving or sending data or power, transcutaneously.

The invention is also directed to the use of an implantable device for enhancing the hearing of a person, the device comprising a mechanism for receiving sound waves and converting them to electrical signals, a transducer which converts the electrical signals to mechanical vibrations, a mechanism that transmits the mechanical vibrations to an intracranial device and thus via the cerebrospinal fluid, brain, perineural channels, cochlear duct and endolymphatic sac and other routes to the inner ear of a person.

The device can be combined with electronics and can be partially implanted in the head of a person and communicate by a subcutaneous coil with electronics external to the person, the electronics comprising a microphone, a switcher, electronics for signal processing, a battery, and a coil for communicating power and data to the implanted device.

The device can be combined with a system which can be fully implanted in the head of a person, the system comprising an implanted microphone, a battery and electronic switches, signal processing and a subcutaneous coil so that power can be transmitted through an external power source and electronics to the implanted device.

The device can be used as a hearing aid or as a tinnitus masker. The device can be used in association with a cochlear implant. The device can be used in both ears of the person as a bilateral aid to hearing.

The preferred embodiment of the invention comprises: (a) a microphone which converts sound waves to electric signals; (b) a vibrating assembly or transducer driven either electromagnetically or by piezoelectric forces or by other means which converts the electric signals to mechanical waves; (c) a connecting bracket which attaches to the skull over the mastoid cavity and supports the vibrating assembly or transducer; (d) a connecting rod which transfers the sound vibrations to a pad; (e) a pad which impinges the dura mater and transfers the mechanical waves to the dura mater of the interior of the skull; (f) wires which interconnect the vibrating assembly to at least one hermetic housing containing electronics or a battery; and (g) at least one coil for receiving and/or sending data or power, transcutaneously.

BRIEF DESCRIPTION OF DRAWINGS

In drawings which illustrate specific embodiments of the invention, but which should not be construed as restricting the spirit or scope of the invention in any way:

FIG. 1a illustrates an isometric view of the left side of the head of a patient with the mastoid cavity area outlined with a dotted line.

FIG. 1b illustrates an isometric view of the top of the head of a patient with the mastoid cavity area on the left side outlined with a dotted line.

DETAILED DESCRIPTION

Figure 2:
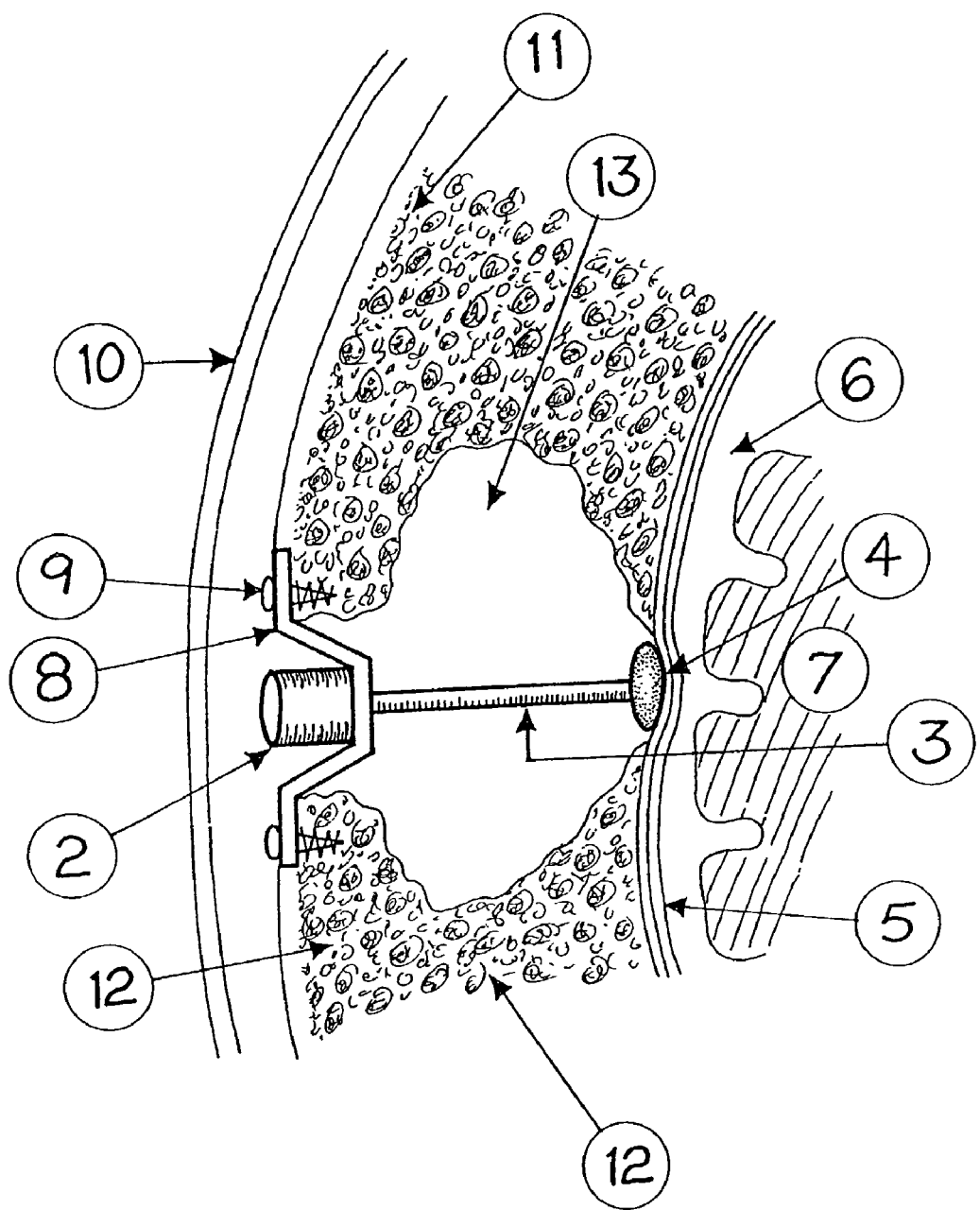
FIG. 2 illustrates a diagrammatic cross section of a preferred embodiment of the device in place in a horizontal section through the mastoid cavity behind the ear.

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Recent advances in knowledge (Freeman S., et al. in Bone conduction experiments in animals—evidence for a non-osseous mechanism, *Hearing Research* 146 (2000) 72–80) demonstrate a hitherto unknown route for sound waves to reach the inner ear via the brain and fluids inside the skull. The subject invention involves transmitting external sound waves to the brain via the dura mater.

The preferred embodiment of the surgically implantable invention comprises:

(a) a microphone which receives sound waves and converts them to electrical signals;

(b) a vibrating assembly or transducer driven either electromagnetically or by piezoelectric forces or by other means which converts the electric signals to mechanical vibrations;

(c) a connecting bracket which attaches to the skull over the mastoid cavity and supports the vibrating assembly or transducer;

(d) a connecting rod which transfers the mechanical vibrations to a pad;

(e) a pad which impinges the dura mater and transfers the mechanical vibrations to the dura mater of the interior of the skull;

(f) a wire which interconnects the vibrating assembly or transducer and the microphone to at least one hermetic housing containing electronics and a battery;

(g) at least one coil for receiving and/or sending data or power, transcutaneously.

A key aspect of the invention is the assembly of the vibrating assembly which is held firmly to the skull on a bracket, and which applies vibration sound waves (mechanical waves) via the connecting rod to the pad against the dura mater and thus to the brain. In certain instances, the rod and pad can be a single mechanism.

The advantages of this device are that it can pick up external acoustical waves and supply them in the form of vibrational sound waves to the dura mater and thus to the cerebrospinal fluid and brain. The sound waves then reach the inner ear by way of the cerebrospinal fluid, and the brain itself, then through presumed channels such as the cochlear duct, the endolymphatic sac and perineural channels.

Surgery provides a simple approach in reaching the dura mater of the patient. A short surgical incision (about 2½ inches) is made in the skin fold of the patient behind the ear, to expose the mastoid bone. A window is drilled in the mastoid bone, and landmarks in the medial wall of the mastoid cavity are identified by the surgeon. A safe site in which to uncover the dura mater is chosen by the surgeon. The device according to the invention is then installed by attaching the bracket to the skull of the patient and adjusting the connecting rod direction and length to thus bring the pad in position against the dura mater of the patient.

An advantage of the invention is that the surgery is simple, it is relatively non-invasive, it avoids any vital structures and there is negligible risk of causing surgical damage to the patient. The invention also benefits from the ease of attachment of the device to different configurations such as (a) a totally internal configuration comprising a microphone, coil, and electronics; (b) a partially implantable device with an external microphone and electronics and RF coil as well as the internal parts; (c) a tinnitus masker; and (d) an attachment in combination with a cochlear implant.

An alternative embodiment of the invention is to attach the device with a modified bracket to the skull of the patient at a location where the skull is close to the brain and is not separated by other structures such as the mastoid air cells, frontal sinus, or intracranial venous sinuses.

In the preferred embodiment, the vibrator is attached to a totally implantable miniature hearing aid system composed of an implanted microphone, electronics in a housing and an RF coil. One embodiment of the components of such a hearing aid system is described in U.S. Pat. No. 6,358,281 BI, the contents of which are incorporated herein by reference.

In the preferred embodiment, the implanted microphone receives and converts external acoustic signals to electric current signals. These electric current signals are sent by wires to a subcutaneous housing over the lateral side of the skull. The housing contains electronics, controls, a battery and switches. The electric current signals are then sent by wires to the transducer on the bracket. The electric current signals are converted to corresponding mechanical vibrations which are transmitted through the rod to the pad and thus to the dura mater of the patient. The mechanical vibrations are propagated through the cerebrospinal fluid and brain to the cochlea through channels presumed to be the vestibular and cochlear aqueduct and the perineural spaces.

In a further alternative embodiment, the electronics can be replaced by those which are suitable as a tinnitus masker.

In a yet further alternative embodiment, both a totally implantable hearing aid and a tinnitus masker can be included.

In still a further alternative embodiment, a cochlear implant can be implanted using the same surgical procedure as described above.

In yet a further alternative embodiment, the battery, switches, electronics and microphone can be external to the patient and communicate by RF linking coils, one subcutaneous with magnet for alignment and one external for communication of data and power.

The vibrator in this device is suitable for use any conventional microphone technology including electromagnetic with moving coil, or piezoelectric. An important element of this invention is the application of the vibrator, bracket, rod, and pad to the patient, such that the external sound waves are transmitted to the dura mater, the cerebrospinal fluids and the brain of the patient. Using this route to the inner ear of the patient provides a simple safe surgical approach to alleviating hearing problems of the patient.

FIG. 1a illustrates an isometric left side view of the head of a patient with the mastoid location 1 indicated in dotted lines. This is a preferred location for implanting the device according to the invention. The preferred embodiment of the device by taking advantage of commercially available microelectronics is small and designed to work in the area of the mastoid air cells.

FIG. 1b illustrates an isometric plan view of the head with the mastoid location 1 indicated by dotted lines.

FIG. 2 illustrates an enlarged diagrammatic cross section of a preferred embodiment of the device installed in a horizontal section through the mastoid cavity 13 behind the ear. FIG. 2 shows the device in place after surgical implantation. A transducer in a hermetic casing 2 picks up acoustical waves via the microphone (not shown) and is the source of the vibrations, which are transmitted through the rod 3 to a pad 4, which lies against the dura mater 5 of the patient and thus delivers the acoustic waves via the dura mater to the cerebrospinal fluid 6 and ultimately the brain 7. The transducer 2 in its casing is held in place on the surface of the mastoid cells 12 by a bracket 8 and screws 9. For completeness of illustration, some anatomical details are shown in FIG. 2, namely the skin 10, the bone of the skull 11 the surrounding mastoid air cells 12 and the mastoid cavity 13. It will be understood that the surgical cavity 13 shown in FIG. 2 has been enlarged for illustrative purposes and, in practice, is not as large as shown in FIG. 2. In practice, the cavity 13 is in the form of a hollow hemisphere, and of sufficient size to house the casing 2, rod 3 and pod 4.

Figure 3:
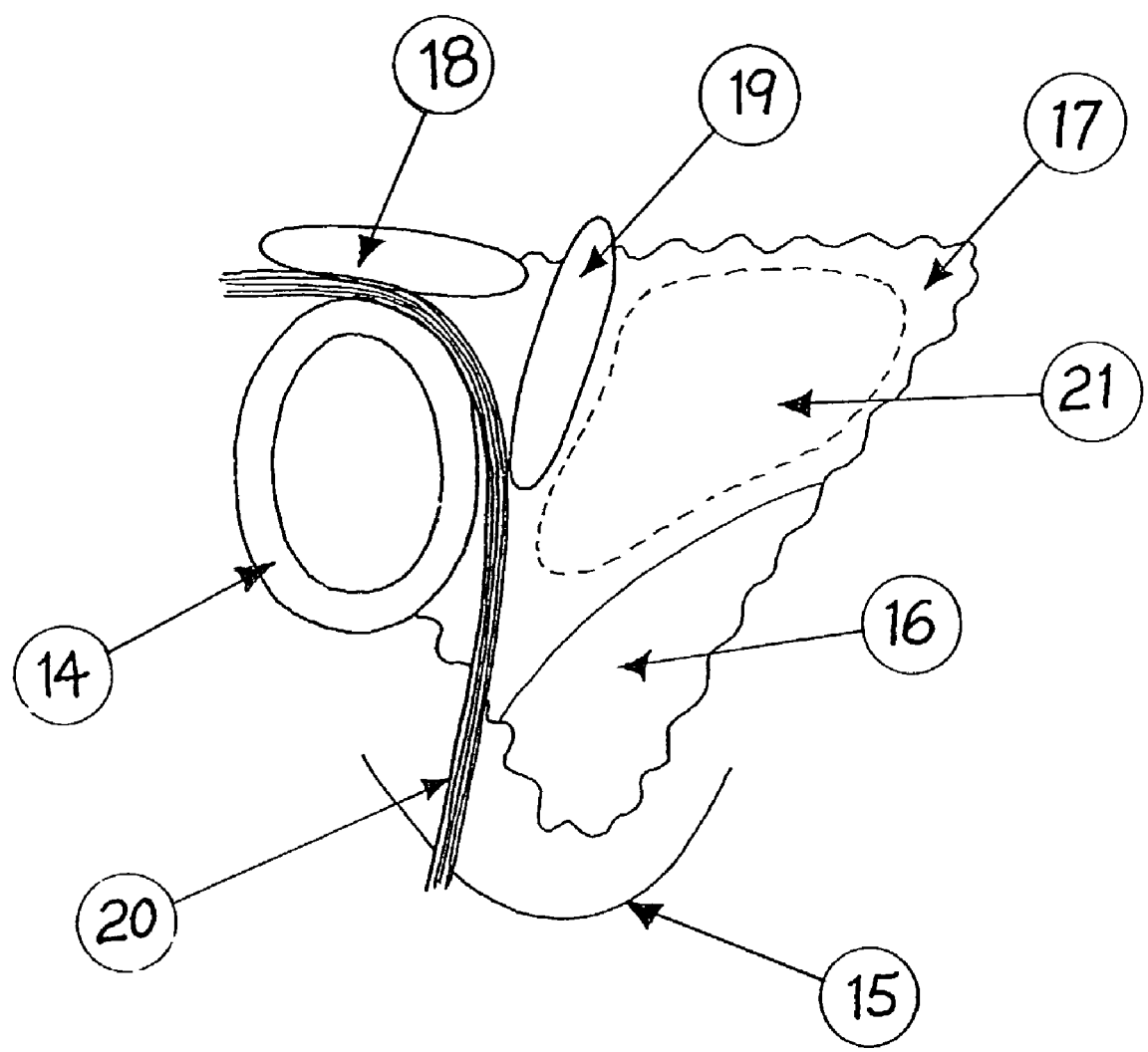
FIG. 3 illustrates a diagrammatic representation of the anatomy of the medial view of the external ear canal and the mastoid cavity.

FIG. 3 represents a view of the medial wall of the surgical area of the left ear and surroundings in diagrammatic form. To clarify the landmarks, and for illustrative purposes, it is expanded as if there has been some removal of bone. The external auditory canal 14 is shown and also the mastoid bone tip 15, the area of the lateral sinus 16, the sino-dural angle 17, the horizontal semicircular canal 18, the posterior semicircular canal 19 and the facial nerve 20. An area 21 has been outlined in dotted lines in which the dura mater may be exposed by a surgeon skilled in the art, with considerable safety, thus providing access of the pad 4 of the device to the dura mater without compromising any other significant anatomical structures.

Figure 4:
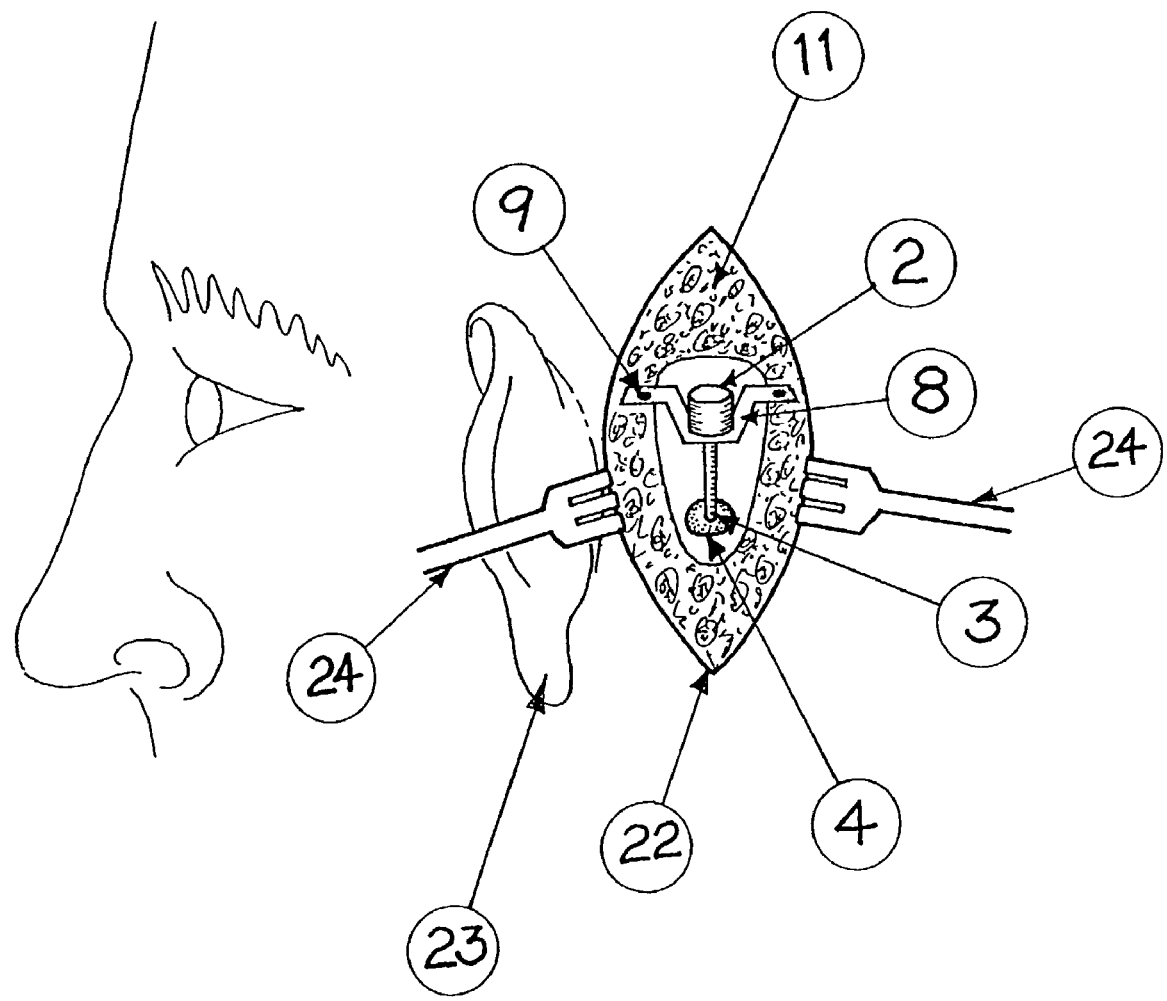
FIG. 4 illustrates an isometric left side view of the head of a patient and a diagrammatic representation of the surgical approach to the mastoid cavity and dura mater with the preferred embodiment of the implant in place. The device has been rotated slightly with the pad down to clarify the view of it.

FIG. 4 illustrates an isometric left side view of the head of a patient and the surgical approach to the mastoid cavity and dura mater with the preferred embodiment of the implant in place. FIG. 4 specifically illustrates the application with a vertical surgical incision 22 made behind the left ear 23 of the patient. The skin is retracted with retractors 24 to expose the device in its surgical position. For clarity, the device is shown rotated slightly down to show the bracket 8 and screws 9, which hold the bracket to the bone of the skull 11 and the transducer in its hermetically sealed casing 2. Also shown are the rod 3 and the pad 4 against the dura mater. It is understood that the rod 3 and pad 4 can be a single unit. The key to the invention is to transmit external acoustic waves to the dura mater by some suitable mechanism.

Figure 5:
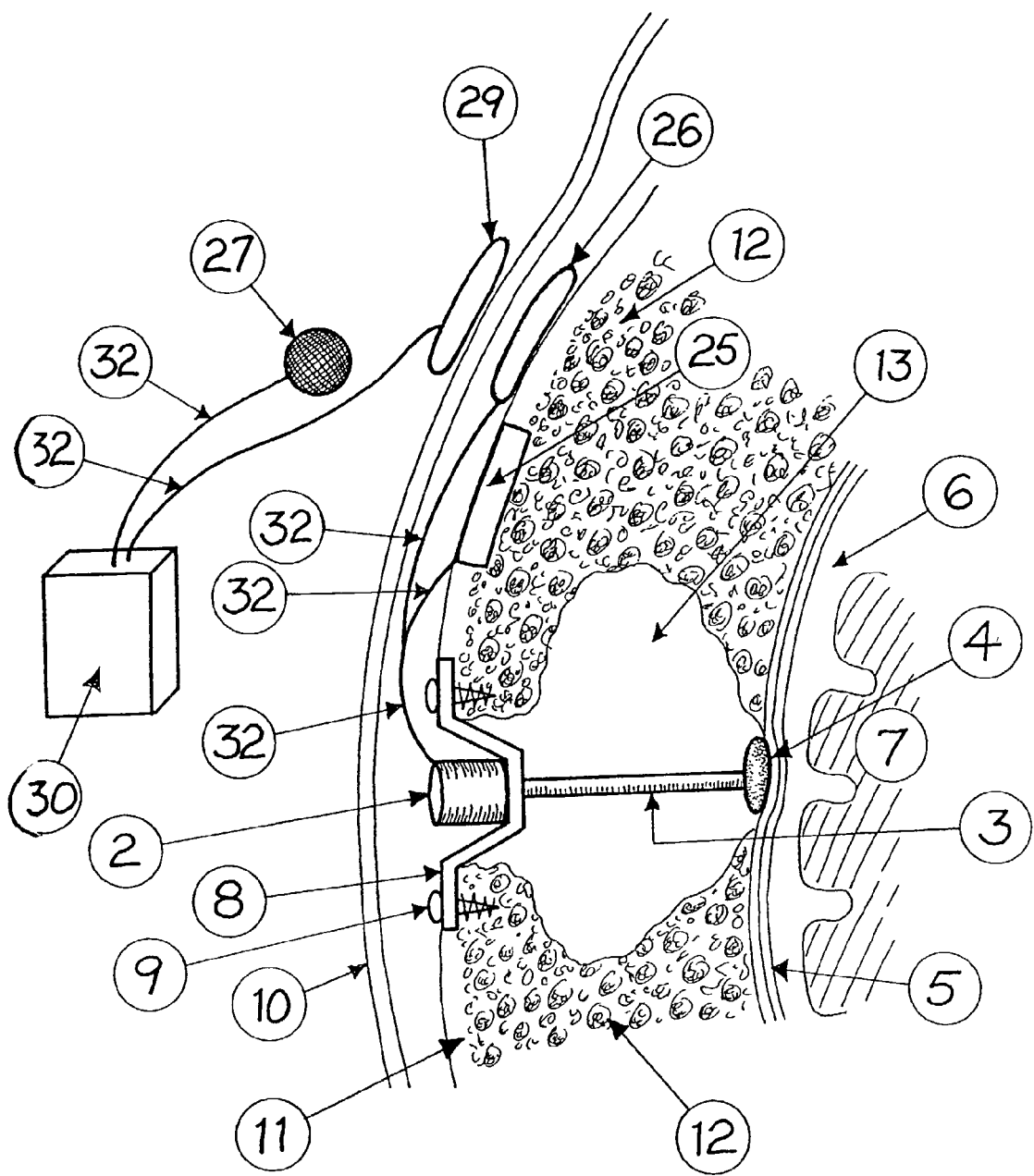
FIG. 5 illustrates a partial section view of the left side of the patient's head with the partially implantable aid consisting of the preferred embodiment of the device connected to a housing and electronics implanted in the skull and a radio frequency coil placed in a subcutaneous position over the skull.

FIG. 5 shows in cross-section enlarged view one of the embodiments of the invention. In particular, FIG. 5 illustrates a partial section-view of the left side of the patient's head with the partially implantable hearing aid consisting of the preferred embodiment of the device connected to a housing and electronics implanted in the skull and a radio frequency coil 26 placed in a subcutaneous position over the skull of the patient. This coil 26 communicates with an external coil 29 by electromagnetic waves. Coil 29 is attached to a housing 30 which contains a battery and signal processing electronics, and also a microphone 27. To accommodate the implantable device (2, 3 and 4), the mastoid cavity 13 has been enlarged by the surgeon by drilling the mastoid air cells. The transducer is shown in its hermetically sealed casing 2 on a bracket 8 held by screws 9 to the exterior bone of the skull 11 of the patient. A rod 3 connects the casing 2 to the pad 4, which is touching the dura mater 5. The electronics for the transducer in the casing 2 are contained in a hermetically sealed casing 25 embedded in the surface of the skull. This communicates with the RF coil 26 under the skin 10 and allows communication with and power delivery by the external components. These external components comprise an external microphone 27, which receives external sound waves, and appropriate electronics, battery and switches housed in a casing 30 which in turn is connected to external RF coil 29. In operation, the microphone 27, having picked up the acoustical sound, is subjected to electronic signal processing by the electronics in casing 30 and is communicated by the RF links to the device at its transducer in casing 2, which converts the electronic signals to corresponding mechanical vibrations, which are then transmitted by the rod 3 to the pad 4, and then the dura mater 5, cerebrospinal fluid 6 and brain 7 whereby it reaches the inner ear of the patient. The transducer and all the electronic parts and the microphone 27 are joined together by wires 32.

Figure 6:
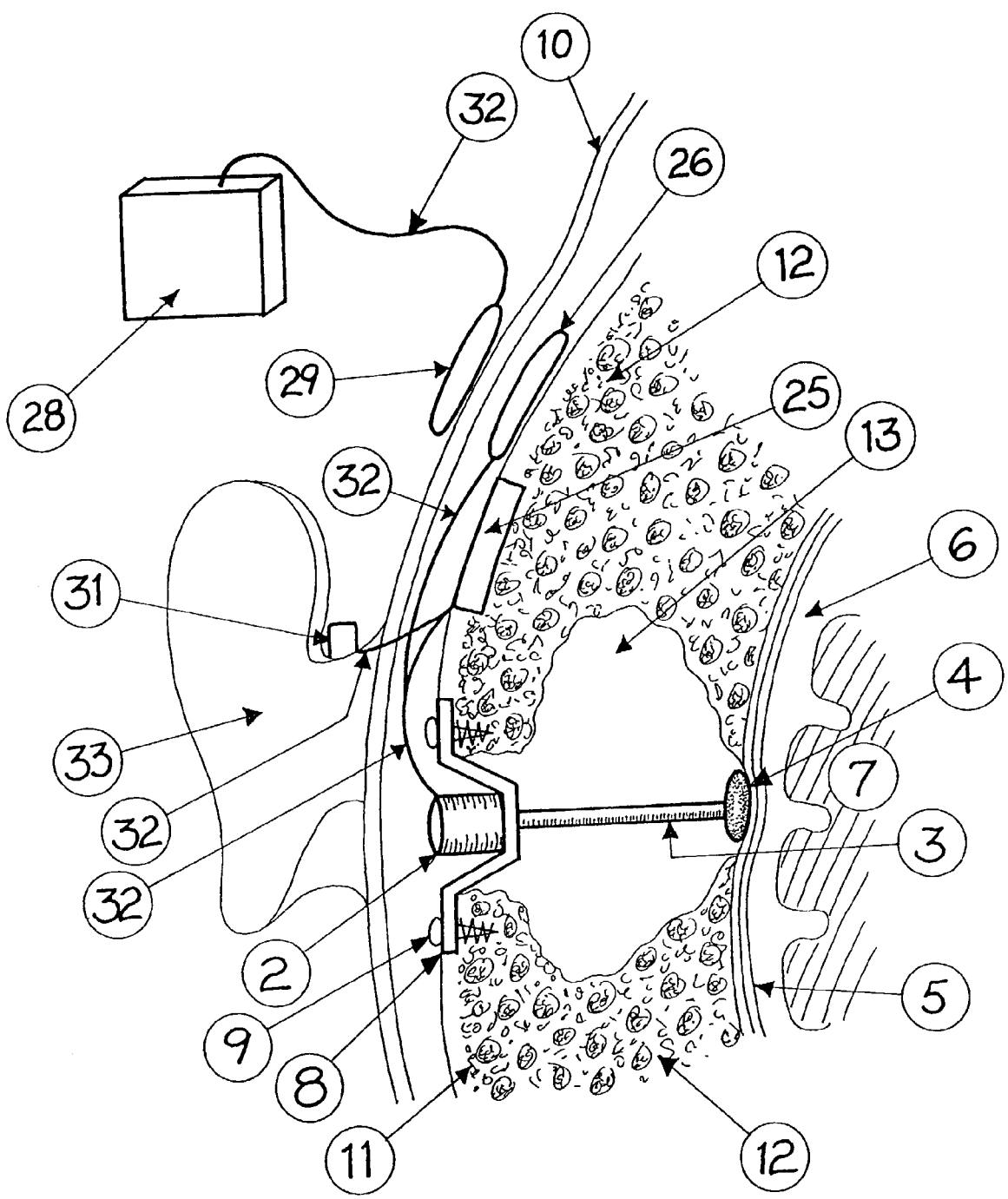
FIG. 6 illustrates an alternative second embodiment of the invention with an internal microphone, an internal battery and electronics, and a coil to allow recharging the battery and switching control of the electronics through an external apparatus.

FIG. 6 shows a further embodiment of the invention with an internal rather than external microphone, an internal battery and electronics, and a coil to allow of recharging the battery and switching control of the electronics through an external apparatus. As seen in FIG. 6, the device is totally implanted and the external electronics in casing 28 merely serve to recharge the internal battery and adjust the internal electronic switching 25 via an external coil 29 and an internal coil 26 is located under the patient's skin 10. The microphone 31 is located internally and in one embodiment it is positioned in the external ear canal 33. The microphone 31 picks up sound, which is processed in the electronics that are contained within the hermetically sealed container 25 and transmitted electronically to the transducer in casing 2 that is held in the skull 11 by a bracket 8 and screws 9. The transducer converts the electronic signals to corresponding mechanical vibrations which are transmitted through the rod 3 which passes through the mastoid cavity 13, which has been surgically enlarged by excision of some mastoid air cells 12, and then to the pad 4, which impinges the dura mater 5. These components drive the sound waves through the dura mater 5 to the cerebrospinal fluid 6 and brain 7 and ultimately, by means unknown, to the inner ear. The transducer and all the electronic parts and the microphone are joined together by wires 32 as indicated.

Figure 7:
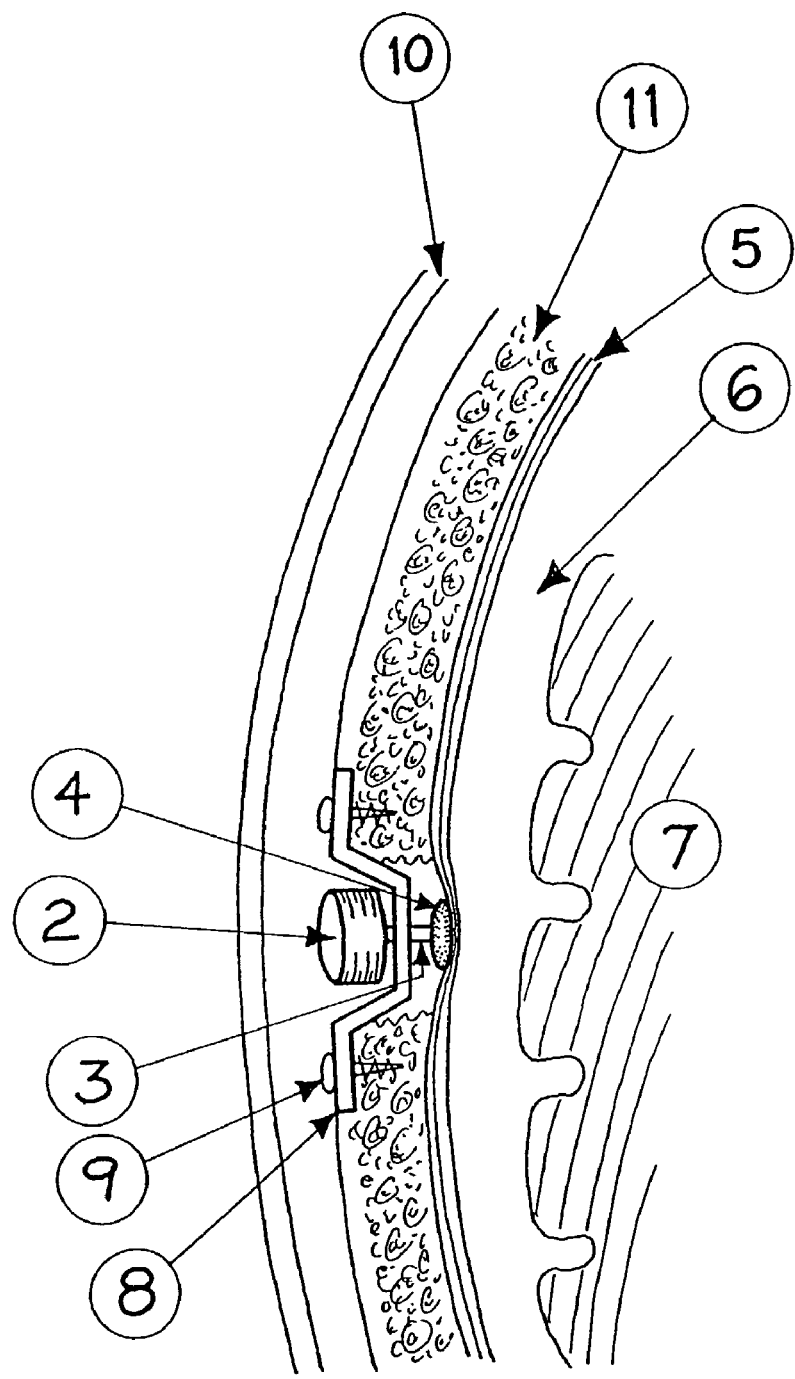
FIG. 7 illustrates a third embodiment in which the device is placed through the skull to make contact directly with the dura mater, without crossing the mastoid or other air space.

FIG. 7 illustrates yet a further embodiment of the invention in which the device is placed within a selected part of the skull other than the mastoid area or the frontal sinus or the intracranial venous sinuses, such that the dura mater 5 is directly within the skull 11 underlying the surgical excavation and not separated by any other structure. FIG. 7 shows the key elements of the device placed in such a location under the skin 10 and in a cavity surgically constructed in the skull 11. In this case the transducer in casing 2 is connected to a rod 3 and this in turn to a pad 4. The bracket 8 is affixed to the skull by screws 9 and is shallower to accommodate this location and is set beneath the skin 10. Sound waves are picked up and transferred from the transducer in casing 2 down the rod 3 to the pad 4 and then transferred through the dura mater 5 to the cerebrospinal fluid 6 and the brain 7 as discussed above.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of enhancing the hearing of a human being, the method comprising detecting ambient sound waves exterior to the head of the human being, converting the sound waves to corresponding electrical signals, converting the electrical signals to mechanical vibrations, and transmitting the mechanical vibrations directly to the dura mater of the interior of the mastoid area of the head of the human being.

2. The method claimed in claim 1 including a member which contacts the dura mater and transmits the mechanical vibrations directly to the dura mater.

* * * * *